United States Patent [19]

Quallich

[11] Patent Number: 5,750,794
[45] Date of Patent: May 12, 1998

[54] PROCESS FOR PREPARING CHIRAL TETRALONE

[75] Inventor: George J. Quallich, North Stonington, Conn.

[73] Assignee: Pfizer Inc., New York, N.Y.

[21] Appl. No.: 652,485

[22] PCT Filed: Sep. 2, 1994

[86] PCT No.: PCT/IB94/00263

§ 371 Date: May 29, 1996

§ 102(e) Date: May 29, 1996

[87] PCT Pub. No.: WO95/15299

PCT Pub. Date: Jun. 8, 1995

Related U.S. Application Data

[63] Continuation of Ser. No. 159,156, Nov. 30, 1993, abandoned.

[51] Int. Cl.$^6$ .................................................. C07C 45/39
[52] U.S. Cl. ...................... 568/322; 568/808; 568/814
[58] Field of Search .......................... 568/808, 814, 568/322

[56] References Cited

U.S. PATENT DOCUMENTS

| | | | |
|---|---|---|---|
| 4,536,518 | 8/1985 | Welch, Jr. et al. | 514/647 |
| 4,556,676 | 12/1985 | Welch, Jr. et al. | 514/554 |
| 4,772,752 | 9/1988 | Brown et al. | |
| 4,777,288 | 10/1988 | Quallich et al. | 562/491 |
| 4,839,104 | 6/1989 | Quallich et al. | 260/396 R |
| 4,943,653 | 7/1990 | Corey | 546/13 |
| 5,019,655 | 5/1991 | Adrian | 568/322 |
| 5,082,970 | 1/1992 | Braish | 564/424 |
| 5,100,901 | 3/1992 | Sugimoto et al. | 514/319 |
| 5,189,177 | 2/1993 | Blacklock et al. | 548/405 |
| 5,196,607 | 3/1993 | Quallich | 568/327 |

FOREIGN PATENT DOCUMENTS

| | | |
|---|---|---|
| 305180 | 3/1989 | European Pat. Off. |
| 9323804 | 11/1993 | WIPO |

OTHER PUBLICATIONS

Begue et al., "Asymmetric Microbial Reduction of Tetralones," *J. Chem. Soc. Perkin Trans.*, 1, pp. 3141–3144 (1992).

Brown et al., "Chiral Synthesis via Organoboranes. 14. Selective Reductions. 41. Diisopinocampheylchloroborane, an Exceptionally Efficient Chiral Reducing Agent," *J. Am. Chem. Soc.*, 110, pp. 1539–1546 (1988).

Corey et al., "Enantioselective Total Synthesis of Bilobalide, A $C_{15}$Ginkgolide," *Tetrahedron Letters*, 29, No.28, pp. 3423–3426 (1988).

Corey et al., "Highly Enantioselective Borane Reduction of Ketones Catalyzed by Chiral Oxazaborolidines. Mechanism and Synthetic Implications," *J. Am. Chem. Soc.*, 109, pp. 5551–5553 (1987).

Corey et al., "Total Synthesis of a $C_{15}$Ginkgolide. (+)-Bilobalide," *J. Am. Chem. Soc.*, 109, pp. 7534–7536 (1987).

Corey et al., "An Efficient and Catalytically Enantioselective Route to (S)-(-)-Phenyloxirane," *J. Org.Chem.*, 53, pp. 2861–2863 (1988).

Midland et al., "Asymmetric Reductions of Prochiral Ketones With B-3-Pinanyl-9-borabicyclo[3.3.1]nonane (Alpine-Borane) at Elevated Pressures," *J. Org. Chem.*, 54, pp. 159–165 (1989).

Midland et al., "Asymmetric Reductions of Propargyl Ketones," *Tetrahedron*, 40, No. 8, pp. 1371–1380 (1984).

Quallich et al., "Friedel–Crafts Synthesis of 4-(3, 4-Dichlorophenyl)-3,4-dihydro-1(2H)-naphthalenone, a Key Intermediate in the Preparation of the Antidepressant Sertraline," *J. Org. Chem.*, 55, No. 16, pp. 4971–4973 (1990).

Quallich et al., "Synthesis of 4(S)-(3,4-Dichlorophenyl)-3, 4-dihydro-1(2H)-naphthalenone by SN2 Cuprate Displacement of an Activated Chiral Benzylic Alcohol," *Tetrahedron*, 48, No. 47, pp. 10239–10248 (1992).

Singh, "Practical and Useful Methods for the Enantioselective Reduction of Unsymmetrical Ketones," *Synthesis*, pp. 605–617 (1992).

Stork et al., "Radical Cyclization–Trapping in the Synthesis of Natural Products. A Simple, Stereocontrolled Route to Prostaglandin $F_{2a}$," *J. Am. Chem. Soc.*, 108, pp. 6384–6385 (1986).

Tremaine et al., "Metabolism and Disposition of the 5-Hydroxytryptamine Uptake Blocker Sertraline in the Rat and Dog," *Drug Metabolism and Disposition*, 17, No. 5, pp. 542–550 (1989).

Weijlard et al., "Preparation of the Stereoisomeric α, β-Diphenyl-β-Hydroxyethylamines," *J. Org. Chem.*, 73, pp. 1216–1218 (1951).

Welch et al., "Nontricyclic Antidepressant Agents Derived from cis–and trans–1–Amino–4–aryltetralins," *J. Med. Chem.*, 27, No. 11, pp. 1508–1515 (1984), and.

Williams et al., "Sertraline: Development of a Chiral Inhibitor of Serotonin Uptake," *Chem. & Rnd.*,(1990).

*Primary Examiner*—James H. Reamer
*Attorney, Agent, or Firm*—Peter C. Richardson; Paul H. Ginsburg; Raymond M. Speer

[57] ABSTRACT

A process for preparing the chiral (4S)-(3,4-dichlorophenyl)-3,4-dihydro-1(2H)-naphthalenone is disclosed wherein racemic 4-(3,4-dichlorophenyl)-3,4-dihydro-1(2H)-naphthalenone is asymmetrically reduced by contacting the racemic tetralone with an asymmetric reagent to produce a mixture of cis and trans alcohols, separating the cis from the trans alcohols, and oxidizing the (4S) enantiomer of the resulting cis and trans alcohols. Also disclosed are novel intermediates used in the synthesis of the above chiral tetralone.

18 Claims, No Drawings

PROCESS FOR PREPARING CHIRAL TETRALONE

REFERENCE TO RELATED APPLICATIONS

This application is a continuation of application U.S. Ser. No. 08/159,156 filed Nov. 30, 1993, now abandoned; and is a U.S. national stage application filed pursuant to the provisions of 35 U.S.C. § 317, based on PCT Application No. PCT/IB94/00263, filed Sep. 2, 1994.

BACKGROUND OF THE INVENTION

The present invention relates to a novel process for asymmetrically reducing racemic 4-(3,4-dichlorophenyl)-3,4-dihydro-1(2H)-naphthalenone (hereinafter also referred to as "the tetralone" or "the racemic tetralone") and for preparing chiral (4S)-(3,4-dichlorophenyl)-3,4-dihydro-1(2H)-naphthalenone (hereinafter also referred to as "the chiral tetralone"), which has utility as an intermediate in the production of pure cis-(1S)(4S)-N-methyl-4-(3,4-dichlorophenyl)-1,2,3,4-tetrahydro-1-naphthaleneamine (sertraline). Sertraline is a known antidepressant agent. This invention also relates to novel intermediates in the synthesis of chiral tetralone.

Several documents relate to the synthesis of pure racemic N-methyl4-(3,4-dichlorophenyl)-1,2,3,4-tetrahydro-1-naphthaleneamine starting with 3,4-dichlorobenzophenone and proceeding via racemic (±)-4-(3,4-dichlorophenyl)-4-butanoic acid and then to (±)-4-(3,4-dichlorophenyl)-3,4-dihydro-1(2H)-naphthalenone. See, e.g., U.S. Pat. No. 4,536,518 (Aug. 20, 1985); U.S. Pat. No. 4,556,676 (Dec. 3, 1985); U.S. Pat. No. 4,777,288 (Oct. 11, 1988); and U.S. Pat. No. 4,839,104 (Jun. 13, 1989); and *Journal of Medicinal Chemistry*, Vol. 27, No. 11, p. 1508 (1984).

*Tetrahedron*, Vol. 48, No. 47, pp. 10239–10248 (1992) relates to a process for preparing the (4S)-enantiomer of 4-(3,4-dichlorophenyl)-3,4-dihydro-1(2H)-naphthalenone comprising reducing the 4-ketobutanoic acid ester with a carbonyl reducing agent, as outlined in E. J. Corey et al., *Journal of Organic Chemistry*, Vol. 53, p. 2861 (1988), to ultimately afford chiral tetralone.

Other asymmetric methods of synthesis have been employed in the art, such as those described by W. M. Whitesides et al., *Journal of the American Chemical Society*, Vol. 91, No. 17, p. 4871 (1969); K. Mori et al., *Synthesis*, p. 752 (1982); B. H. Lipshutz et al., *Journal of Organic Chemistry*, Vol. 49, p. 3928 (1984); B. H. Lipshutz et al., *Journal of the American Chemical Society*, Vol. 104, p. 4696 (1982); G. M. Whitesides et al., *Journal of the American Chemical Society*, Vol. 91, No. 17 (1969); C. R. Johnson et al., *Journal of the American Chemical Society*, Vol. 95, No. 23, p. 7783 (1973); B. H. Lipshutz et al., *Tetrahedron*, Vol. 40, No. 24, p. 5005 (1984); and C. R. Johnson et al., *Journal of the American Chemical Society*, Vol. 95, No. 23, p. 7777 (1973).

All of the documents cited herein, including the foregoing, are incorporated herein in their entireties.

SUMMARY OF THE INVENTION

Broadly, the present invention relates to a process for asymmetrically reducing racemic 4-(3,4-dichlorophenyl)-3,4-dihydro-1(2H)-naphthalenone comprising reacting the racemic 4-(3,4-dichlorophenyl)-3,4-dihydro-1(2H)-naphthalenone with an asymmetric ketone reducing agent. The asymmetric ketone reducing agent is preferably a catalytic chiral oxazaborolidine compound.

Preferred chiral oxazaborolidine compounds have the formula:

wherein:

$R^1$ is hydrogen, $(C_1-C_8)$alkyl, benzyl, phenyl or phenyl substituted with up to three substituents independently selected from $(C_1-C_8)$alkyl, $(C_1-C_8)$alkoxy and halo; and $R^2$1 and $R^3$ are syn and the same and are each phenyl or phenyl substituted with up to three substituents independently selected from $(C_1-C_8)$alkyl, $(C.-C_8)$alkoxy and halo.

Other preferred chiral oxazaborolidine compounds have the formula:

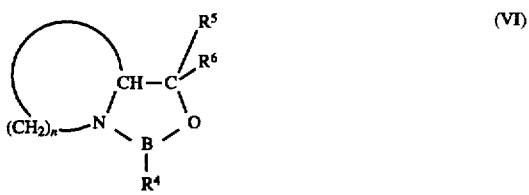

wherein:

$R^4$ is hydrogen, lower alkyl or aralkyl;

n is 2, 3, or 4, such that the group $(CH_2)_n$ forms, together with the oxazaborolidine nitrogen and adjacent carbon, a 4-, 5- or 6-membered ring; and $R^5$ and $R^6$ are phenyl.

Another preferred asymmetric ketone reducing agent comprises either enantiomer of the compound having the formula:

$Ipc_2BX$ wherein Ipc is isopinocampheyl, B is boron and X is halo.

The reduction of the racemic tetralone, depending on the asymmetric ketone reducing agent chosen, will yield either cis and trans alcohols having the following formulae:

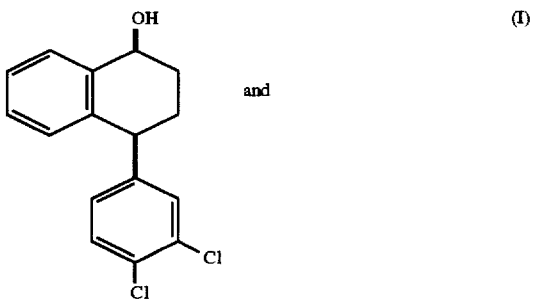

and

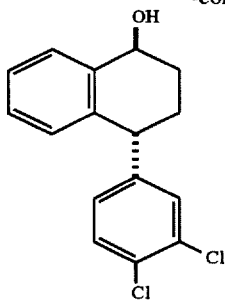

or cis and trans alcohols having the following formulae:

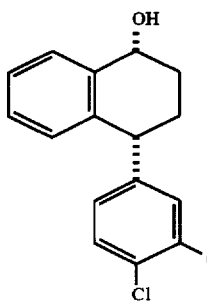 (IV)

and

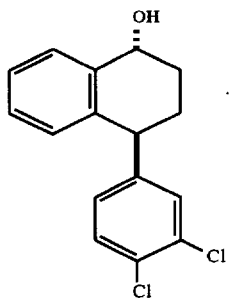 (II)

The enantiomer of the asymmetric reducing agent determines whether (I) and (III) or (II) and (IV) is produced.

The present invention also relates to each of the two reduction processes described above (i.e., that which produces compounds (I) and (III) and that which produces compounds (II) and (IV)), further comprising separating, respectively, the cis alcohol (I) from the trans alcohol (III) or the cis alcohol (IV) from the trans alcohol (II) and oxidizing, respectively, the resulting cis alcohol (I) or trans alcohol (II) to produce chiral tetralone.

The present invention also relates to a process comprising reacting racemic tetralone with an asymmetric ketone reducing agent to produce compounds having the formulae:

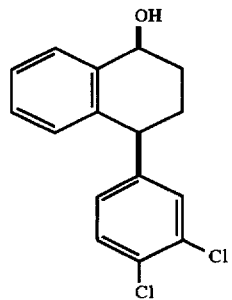 (I)

and

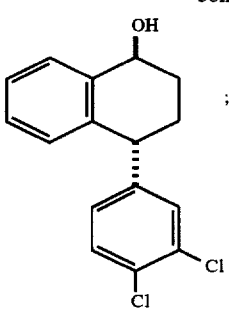 (III)

or compounds having the formulae:

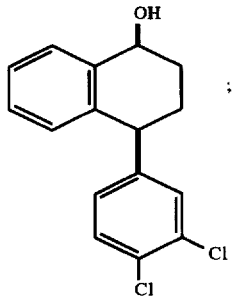 (II)

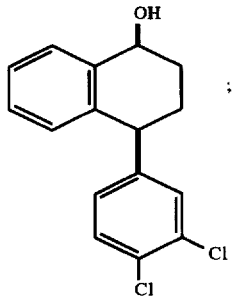 (IV)

said process further comprising the steps of oxidizing the compounds having, respectively, formula (III) or (IV) to produce the 4(R) enantiomer of the tetralone ((4R)-(3,4-dichlorophenyl)-3,4-dihydro-1(2H)-naphthalenone), and contacting the resulting 4(R) tetralone with a base to produce racemic tetralone.

The present invention also relates to compounds having the following formulae:

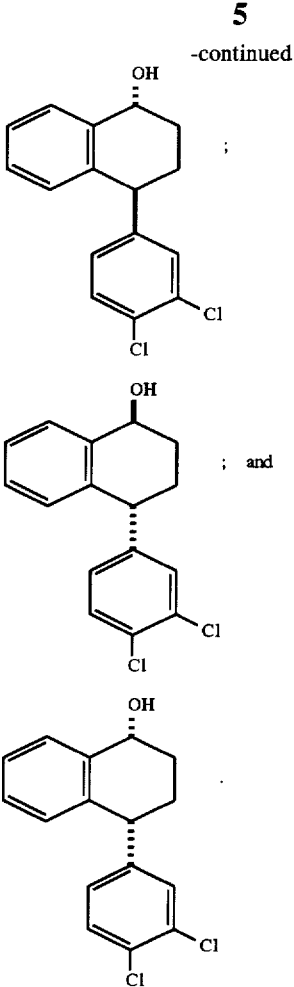

The term "halo", as used herein, unless otherwise indicated, includes chloro, fluoro, bromo and iodo.

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is defined as above.

The term "aralkyl", as used herein, includes aryl groups, wherein "aryl" is defined as below, terminating in an alkyl group, as defined above, which is the point of attachment.

The term "aryl", as used herein, means mononuclear aromatic hydrocarbon groups such as phenyl, which can be unsubstituted or substituted in one or more positions, and polynuclear aryl groups such as naphthyl, anthryl, phenanthryl, and so forth, which can be unsubstituted or substituted with one or more groups.

The term "one or more substituents", as used herein, includes from one to the maximum number of substituents possible based on the number of available bonding sites.

DETAILED DESCRIPTION OF THE INVENTION

The processes of this invention for preparing the chiral tetralone (4S)-(3,4-dichlorophenyl)-3,4-dihydro-1(2H)-naphthalenone are depicted in the following reaction schemes:

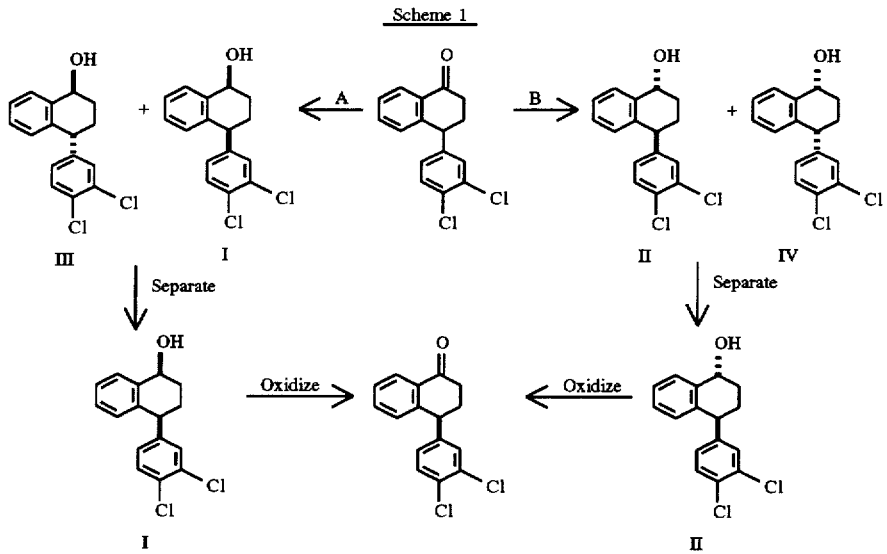

Scheme 2

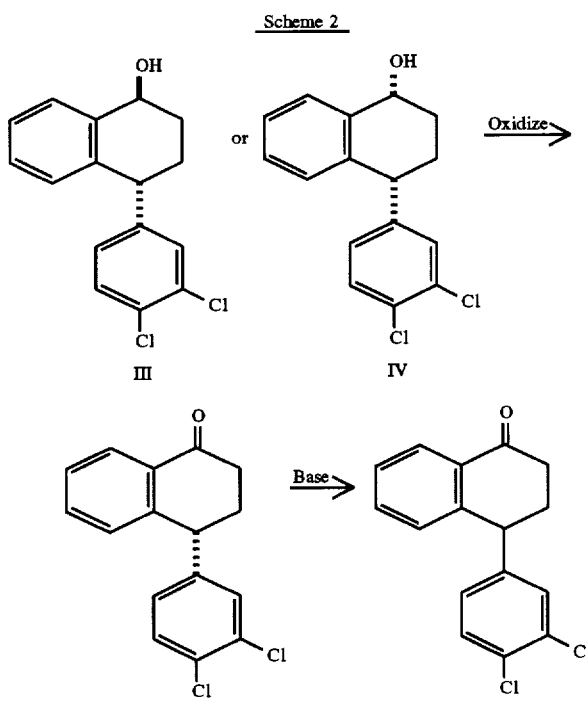

Referring to Scheme 1, racemic 4-(3,4-dichlorophenyl)-3,4-dihydro-1(2H)-naphthalenone (tetralone) is asymmetrically reduced by reacting the racemic tetralone with an asymmetric reagent (A) or (B), wherein (A) and (B) are enantiomers. Reduction of racemic tetralone with enantiomer A yields compounds of formulae I and III. Reduction of racemic tetralone with enantiomer B yields compounds of formulae II and IV.

The reduction is performed in a suitable solvent such as tetrahydrofuran, toluene, or an alternative etherial solvent. The reduction is performed at a temperature of from about −20° C. to about 50° C., preferably from 20° C. to 25° C. The ratio of racemic tetralone to asymmetric reagent is from about 1.0:0.025 to about 1.0:1.5. When the asymmetric reagent is a compound of formula (V), (Va) or (VI), then the ratio of racemic tetralone to asymmetric reagent is preferably from about 1.0:0.025 to about 1.0:0.1. When the asymmetric reagent is a compound of formula Ipc$_2$BX, then the ratio of racemic tetralone to asymmetric reagent is preferably from about 1.0:1.0 to about 1.0:1.5.. The asymmetric reduction of racemic tetralone produces a mixture of cis and trans alcohols of the formulae (I) and (III) or of the formulae II and IV depending upon the chirality of the asymmetric reagent employed. The cis alcohol (I) can be separated from the trans alcohol (III) by methods known in the art, such as chromatography. Similarly, the trans alcohol II can be separated from the cis alcohol IV by methods known in the art. In each case, the desired product possesses the chirality desired for sertraline. The (4S) tetralone can be prepared by Jones oxidation, Swern oxidation, Manganese dioxide, pyridium chlorochromate, and pyridium dichromate of the resulting cis alcohol (I) and trans alcohol (II).

Examples of suitable asymmetric reducing reagents include chiral oxazaborolidine compounds of the formula:

wherein $R^1$ is hydrogen, ($C_1$–$C_8$)alkyl, benzyl, phenyl or phenyl substituted with up to three substituents independently selected from ($C_1$–$C_8$)alkyl, ($C_1$–$C_8$)alkoxy or halo; and $R^2$ and $R^3$ are syn and the same and are each phenyl or phenyl substituted with up to three substituents independently selected from ($C_1$–$C_8$)alkyl, ($C_1$–$C_8$)alkoxy or halo groups such as chloro or fluoro. A preferred number of substituents is zero. A preferred group of such compounds is the group of compounds wherein $R^1$, $R^2$ and $R^3$ are all unsubstituted phenyl. Especially preferred is the compound wherein $R^2$ and $R^3$ are each unsubstituted phenyl and $R^1$ is methyl. Also, especially preferred is the compound wherein $R^2$ and $R^3$ are each phenyl and $R^1$ is hydrogen.

Suitable asymmetric reagents also include a chiral 1,3,2-oxazaborolidine of the formula:

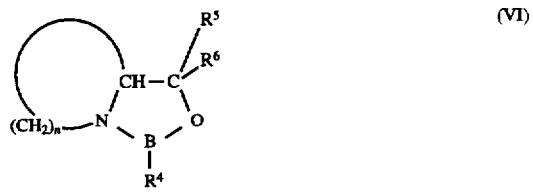

in which: $R^4$ is hydrogen, lower alkyl or aralkyl; n is 2, 3, or 4, such that the group $(CH_2)_n$ forms, together with the oxazaborolidine nitrogen and adjacent carbon, a 4-, 5- or 6-membered ring; and $R^5$ and $R^6$ are phenyl. Aralkyl is as defined above. Preferred alkyl groups of the aralkyl are $CH_2$. Preferred aralkyl groups are phenylalkyl groups.

Suitable asymmetric reagents also include a haloborane represented by the formula: Ipc$_2$BX, wherein Ipc is isopinocampheyl, B is boron and X is halo.

Additional suitable asymmetric reagents are disclosed in U.S. Pat. No. 5,189,177 issued Feb. 23, 1993; U.S. Pat. No. 4,943,635 issued Jul. 24, 1990; U.S. Pat. No. 4,772,752 issued Sep. 20, 1988; U.S. patent application Ser. No. 08/061,895 filed May 14, 1993; International Patent Application PCT/US93/00687, filed Feb. 1, 1993; International Patent Application PCT/US92/05434, filed Jul. 1, 1992; and International Patent Application PCT/US92/05433, filed Jul. 1, 1992.

Referring to Scheme 2, the process for making (4S)-(3,4-dichlorophenyl)-3,4-dihydro-1(2H)-naphthalenone may optionally contain one or more additional steps wherein alcohols (III) and/or (IV) are recycled. In this process, the alcohols (III) and/or (IV) are oxidized to produce 4(R) enantiomer of the tetralone, which is then reacted with a base to produce the racemic tetralone. The oxidation can be done by methods known to those skilled in the art. The racemization reaction is performed at a temperature of from about 0° C. to about 100° C., preferably 25° C. to 65° C. The 4(R) enantiomer of the tetralone is reacted with a base at a temperature of from about 25° C. to about 65° C., preferably 50° C. to 80° C. Suitable bases for this reaction include potassium t-butoxide, sodium hydroxide, sodium methoxide, and potassium hydroxide. A preferred base is potassium t-butoxide.

The (4S)-4-(3,4-dichlorophenyl)-3,4-dihydro-1(2H)-naphthalenone final product afforded by the process of this invention is a valuable intermediate that can be used to synthesize the antidepressant agent known as sertraline or cis-(1S)(4S)-N-methyl4-(3,4-dichlorophenyl)-1,2,3,4-tetrahydro-1-naphthaleneamine by methods disclosed in the previously discussed prior art. More specifically, (4S)-4-(3, 4-dichlorophenyl)-3,4-dihydro-1(2H)-naphthalenone is first converted to (4S)-N-[4-(3,4-dichlorophenyl)-3,4-dihydro-1 (2H)-naphthalenylidine]methanamine and then finally to the desired cis-(1S)(4S)-N-methyl4-(3,4-dichlorophenyl)-1,2,3, 4-tetrahydro-1-naphthaleneamine by the known methods of the prior art process, as earlier described in U.S. Pat. No. 4,536,518 (Aug. 20, 1985). In the present instance, the optically-active ketone, viz., (4S)-4-(3,4-dichlorophenyl)-1 (2H)-naphthalenone, is first reductively aminated to give chiral cis-N-methyl-4-(3,4-dichlorophenyl)-1,2,3,4-tetrahydro-1-naphthaleneamine and the latter product is then separated by chromatographic means to ultimately yield the desired final medicinal product which is sertraline.

The preparation of other compounds of the present invention not specifically described in the foregoing experimental section can be accomplished using combinations of the reactions described above that will be apparent to those skilled in the art.

In each of the reactions discussed or illustrated in Schemes 1 or 2 above, pressure is not critical unless otherwise indicated. Pressures from about 0.9 atmospheres to about 2 atmospheres are generally acceptable and ambient pressure, i.e., about 1 atmosphere, is preferred as a matter of convenience.

The activity, methods for testing activities, dosages, dosage forms, methods of administration and background information concerning sertraline are set forth in U.S. Pat. No. 4,536,518 (Aug. 20, 1985), U.S. Pat. No. 4,777,288 (Oct. 11, 1988), and U.S. Pat. No. 4,839,104 (Jun. 13, 1989), and the *Journal of Medicinal Chemistry*, Vol. 27, No. 11, p. 1508 (1984).

The present invention is illustrated by the following examples. It will be understood, however, that the invention is not limited to the specific details of these examples.

EXAMPLE 1

(4S)-(3,4-dichlorophenyl)-3,4-dihydro-1(2H)-naphthalenone

Borane methylsulfide complex (2M in THF, 6.0 mL, 12 mmol) was added all at once to a solution of (1S,2R)-(+)-erythro-2-amino-1,2-diphenylethanol [*J. Amer. Chem. Soc.* 1216 (1951) also commercially available] (183 mg, 0.86 mmol) In THF (55 mL) under a nitrogen atmosphere. The solution was stirred for 18 hours. Racemic tetralone (5.0 g, 17 mmol) as a solution in THF was added over 1 hour, the reaction stirred 15 minutes after the addition was completed, cooled to 0° C. and quenched with methanol. After stirring the quenched reaction for 18 hours the solvents were removed under vacuum, the contents dissolved in methylene chloride (100 mL), and washed sequentially with pH4 phosphate buffer (100 mL), water (100 mL), treated with magnesium sulfate, and solvent removed to afford a mixture of the cis and trans alcohols (5.01 g). Chromatography with ethyl acetate/hexanes provided the less polar cis alcohol. $^1$H NMR δ (CDCl$_3$) 7.46 (dd, J=1 Hz, J=7 Hz, 1H), 7.41–7.07 (m, 4H), 6.98 (dd, J=2 Hz, J=8 Hz, 1H), 6.82 (d, J=7 Hz, 1H), 4.86 (t, J=4 Hz, 1H), 3.99 (t, J=8 Hz, 1H), 2.18–1.87 (m, 5H). $^{13}$C NMR δ 147.0, 138.9, 138.4, 132.4, 130.7, 130.4, 130.2, 129.8, 129.1, 128.3, 128.2, 127.1, 67.9, 45.1, 30.1, 28.2 and the more polar trans alcohol. $^1$H NMR (CDCl$_3$) δ 7.54 (d, J=7 Hz, 1H), 7.4–7.07 (m, 4H), 6.90–6.75 (m, 2H), 4.88 (t, J=5 Hz, 1H), 4.13 (t, J=6 Hz, 1H), 2.43–1.63 (m, 5H). The less polar cis alcohol 1 (160 mg, 0.546 mmol) was dissolved in methylene chloride (5 mL), treated with pyridium chlorochromate (220 mg, 1.023 mmol), and stirred for 2 hours at ambient temperature. Diethyl ether was added (25 mL), stirred 20 minutes, and the solvent decanted. The residual dark gum was washed with diethyl ether (2×15 mL), the organic layers combined, filtered through a pad of magnesium sulfate, and solvent removed under vacuum to afford a brown oil (170 mg). Chromatography on silica (5.1 g) eluting with methylene chloride provided the chiral tetralone as a clear oil (118 mg). This material was determined to be ≧95% ee by HPLC with a chiral support (Diacel Co. ChiralcelOD 4.6 mm×25 cm, 10% isopropyl alcohol/hexane).

EXAMPLE 2

(4)-(3,4-dichlorophenyl)-3,4-dihydro-1(2H)-naphthalenone (3,4-dichlorophenyl)-3,4-dihydro-1(2H)-naphthalenone ("the tetralone") (5 g, 17 mmol), (S)-Tetrahydro-1-methyl-3,3diphenyl-1H,3H-pyrrolo-[1,2-c][1,3,2]oxazaborole [*J. Org. Chem.* 2861 (1988)] (238 mg, 0.859 mmol), and tetrahydrofuran (THF) (68 mL) were combined at ambient temperature in a flamed dried flask under a nitrogen atmosphere. Borane methylsulfide complex (2M in THF, 4.56 mL) was added over 1 hour, 30 minutes later the reaction was quenched at 0° C. with methanol (16.8 mL), and stirred for 18 hours. The solvents were removed under vacuum, the contents dissolved in methylene chloride (68 mL), and washed sequentially with pH4 phosphate buffer (68 mL), water (68 mL), treated with magnesium sulfate, and solvent removed to afford a mixture of the cis and trans alcohols (4.93 g). Chromatography with ethylacetate/hexanes provided the less polar cis alcohol αD=–52.27 (c=1.01, methylene chloride) and more polar trans alcohol αD=+37.79 (c=1.18, methylene chloride). The more polar trans alcohol 2 (160 mg, 0.546 mmol) was dissolved in methylene chloride (5 mL), treated with pyridium chlorochromate (220 mg, 1.023 mmol), and stirred for 2 hours at ambient temperature. Diethyl ether was added (25 mL), stirred 20 minutes, and the solvent decanted. The residual dark gum was washed with diethyl ether (2×15 mL), the organic layers combined, filtered through a pad of magnesium sulfate, and solvent removed under vacuum to afford a brown oil (162 mg). Chromatography on silica (5 g) eluting with 25% ethyl acetate/hexanes provided the chiral tetralone as a clear oil (139 mg) αD=+36.8 (c=1.11) which corresponds to a 56% ee.

EXAMPLE 3

(4S)-(3,4-dichlorophenyl)-3,4-dihydro-1(2H)-naphthalenone

[(+)-β-chlorodiisopinocampheylborane] (6.07 g, 18.97 mmol) was dissolved in THF (13.6 mL) under a nitrogen atmosphere, and cooled to –25° C. Tetralone (5 g, 17 mmol) was added as a solution in THF (13.6 mL), the contents allowed to warm to ambient temperature, and stirred 46 hours. The solvent was removed under vacuum, diethyl ether (65 mL) and ethanol amine (3.9 mL) were added, and the contents stirred for 18 hours. The precipitate was filtered off, washed with pentane (2×20 mL), and the solvent removed under vacuum from the filtrate to yield the crude product (4.98 g) which was chromatographed on silica with 25% ethyl acetate/hexanes to separate the cis and trans alcohols. The more polar trans alcohol 2 (175 mg, 0.579 mmol) was dissolved in methylene chloride (5 mL) and treated with pyridium chlorochromate (192 mg) for 2 hours at ambient temperature. Diethyl ether was added (25 mL), stirred 15 minutes, and the solvents decanted. The residual black semisolid was washed with diethyl ether (2×10 mL), the organic phases combined, filtered through CELITE, and solvent removed under vacuum to yield the crude chiral tetralone. Chromatography on silica eluting with 25% ethyl acetate/hexanes afforded 165 mg of pure product αD=+ 30.94 (c=1.28, acetone) which corresponds to 47% ee.

EXAMPLE 4

4-(3,4-dichlorophenyl)-3,4dihydro-1(2H)-naphthalenone

Pyridium chlorochromate oxidation of the trans alcohols 3 and 4 with the same procedure employed on alcohols 1 and 2 provided the chiral tetralone. Racemization of the chiral tetralone into racemic tetralone was achieved as follows. Potassium t-butoxide (90 mg, 0.80 mmol) was added to a solution of chiral tetralone (1.12 g, 3.84 mmol) in THF (4 mL). The solution was refluxed for 18 hours under nitrogen, cooled to ambient temperature, methylene chloride (10 mL) and aqueous hydrochloric acid (1N, 20 mL) added, and the phases separated. The organic phase was washed with water (10 mL), brine (10 mL), dried with magnesium sulfate, and solvent removed under vacuum to yield 1.1 g of the crude racemic tetralone. Recrystallization from methanol afforded 1.07 g (95%) of the racemic tetralone mp-104°–5° C. Other base solvent combinations which effect racemization are methanol/sodium methoxide, methanol/sodium hydroxide, and methanol/potassium hydroxide.

I claim:

1. A process for asymmetrically reducing racemic 4-(3,4-dichlorophenyl)-3,4-dihydro-1-(2H)-naphthalenone of Formula (A) below to yield any two or four enantiomeric cis and trans alcohols of Formulas (I) through (IV) below:

A

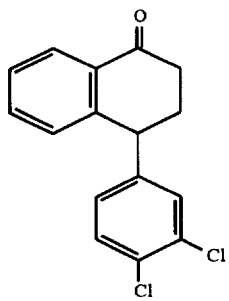

I

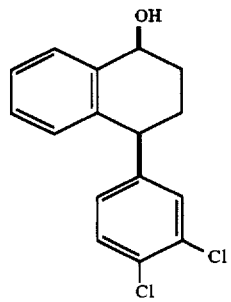

II

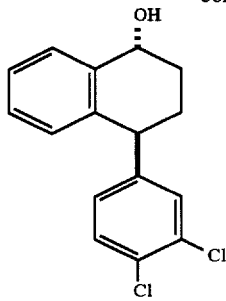

III

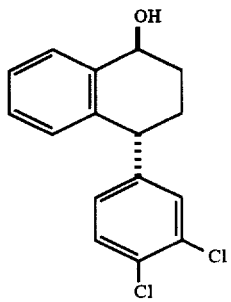

IV

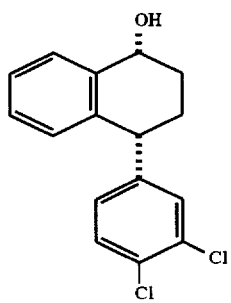

comprising reacting said racemic 4-(3,4-dichlorophenyl)-3,4-dihydro-1(2H)-naphthalenone with one or more asymmetric ketone reducing agents comprising enantioselective organoborane reagents.

2. A process according to claim 1 wherein said enantioselective organoborane reagent is a chiral catalytic oxazaborolidine compound and a source of borane is additionally present.

3. A process according to claim 2 wherein the chiral oxazaborolidine compound has the formula:

 (V)

or

 (Va)

wherein:

$R^1$ is hydrogen, ($C_1$–$C_8$) alkyl, benzyl, phenyl or phenyl substituted with up to three substituents independently selected from ($C_1$–$C_8$)alkyl, ($C_1$–$C_8$)alkoxy and halo; and $R^2$ and $R^3$ are syn and the same and are each phenyl or phenyl substituted with up to three substituents independently selected from $(C_1-C_8)$alkyl, $(C_1-C_8)$alkoxy and halo.

4. A process according to claim 2 wherein the chiral oxazaborolidine compound has the formula:

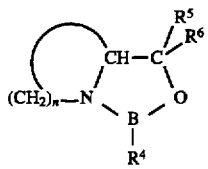

(VI)

wherein:

$R^4$ is hydrogen, lower alkyl or aralkyl;

n is 2, 3, or 4, such that the group $(CH_2)_n$ forms, together with the oxazaborolidine nitrogen and adjacent carbon, a 4-, 5- or 6-membered ring; and $R^5$ and $R^6$ are phenyl.

5. A process according to claim 1 wherein said enantioselective organoborane agent comprises either enantiomer of the compound having the formula:

Ipc₂BX wherein Ipc is isopinocampheyl, B is boron and X is halo.

6. A process for preparing chiral (4S)-(3,4-dichlorophenyl)-3,4-dihydro-1(2H)-naphthalenone of Formula (B) below comprising:

A. asymmetrically reducing racemic 4-(3,4-dichlorophenyl)-3,4-dihydro-1(2H)-naphthalenone of Formula (A) below to yield four enantiomeric cis and trans alcohols of Formulas (I) through (IV) below:

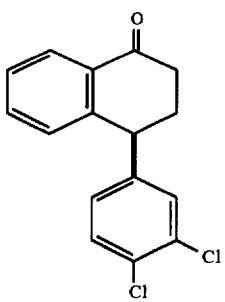

B

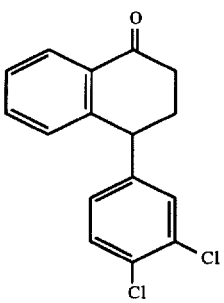

A

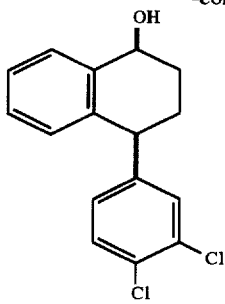

I

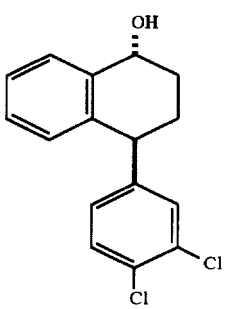

II

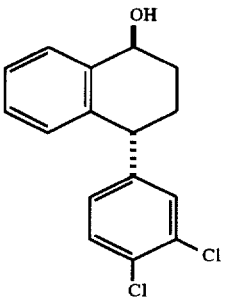

III

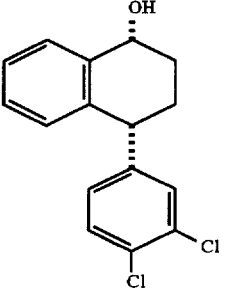

IV by reacting said racemic 4-(3,4-dichlorophenyl)-3,4-dihydro-1(2H)-naphthalenone with one or more asymmetric ketone reducing agents comprising enantioselective organoborane reagents;

B. separating cis alcohol of Formula (I) from trans alcohol of Formula (III) and oxidizing said cis alcohol of Formula (I) to yield said chiral (4S)-(3,4-dichlorophenyl)-3,4-dihydro-1(2H)-naphthalenone of Formula (B);

C. separating cis alcohol of Formula (IV) from trans alcohol of Formula (II) and oxidizing said trans alcohol of Formula (II) to yield said chiral (4S)-(3,4-dichlorophenyl)-3,4-dihydro-1(2H)-naphthalenone of Formula (B).

7. A process according to claim 6 wherein said asymetric ketone reducing agent is a chiral oxazaborolidine having the formula:

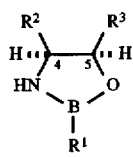

(V)

or

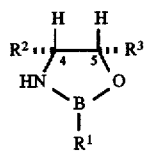

(Va)

wherein:

R¹ is hydrogen, (C₁-C₈) alkyl, benzyl, phenyl or phenyl substituted with up to three substituents independently selected from (C₁-C₈)alkyl, (C₁-C₈)alkoxy and halo; and R² and R³ are syn and the same and are each phenyl or phenyl substituted with up to three substituents independently selected from (C₁-C8)alkyl, (C₁-C₈)alkoxy and halo.

8. A process according to claim 6 wherein said asymmetric ketone reducing agent is a chiral oxazaborolidine having the formula:

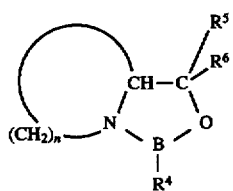

(VI)

wherein:

R⁴ is hydrogen, lower alkyl or aralkyl;

n is 2, 3, or 4, such that the group (CH₂)ₙ, forms, together with the oxazaborolidine nitrogen and adjacent carbon, a 4-, 5- or 6-membered ring; and R⁵ and R⁶ are phenyl.

9. A process according to claim 6 wherein said enantioselective organoborane reagent is a chiral catalytic oxazaborolidine compound and a source of borane is additionally present.

10. A process according to claim 6 wherein said separation of said cis alcohol of Formula (I) from said trans alcohol of Formula (III), and said separation of said cis alcohol of Formula (IV) from said trans alcohol of Formula (II) are both carried out using chromatography.

11. A process according to claim 6 wherein said oxidizing of said cis alcohol of Formula (I) and said oxidizing of said trans alcohol of Formula (II) are carried out using an oxidizing method independently selected from the group consisting essentially of Jones oxidation, Swern oxidation, and oxidation using manganese dioxide, pyridium chlorochromate, or pyridium dichromate.

12. A process according to claim 6, further comprising oxidizing said cis and trans alcohols of Formulas (III) and (IV) to yield chiral (4R)-(3,4-dichlorophenyl)-3,4-dihydro-1(2H)-naphthalenone of Formula (C) below, and reacting said chiral (4R)-(3,4-dichlorophenyl)-3,4-dihydro-1(2H)-naphthalenone of Formula (C) with base to yield said racemic 4-(3,4-dichlorophenyl)-3,4-dihydro-1(2H)-naphthalenone of Formula (A):

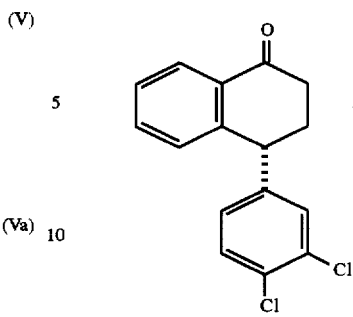

C

13. A process according to claim 12 wherein said base is a member independently selected from the group consisting of potassium t-butoxide, sodium hydroxide, sodium methoxide, and potassium hydroxide.

14. A process for preparing chiral (4S)-(3,4-dichlorophenyl)-3,4-dihydro-1(2H)-naphthalenone of Formula (B) below comprising:

A. asymmetrically reducing racemic 4-(3,4-dichlorophenyl)-3,4-dihydro-1(2H)-naphthalenone of Formula (A) below to yield any two or four enantiomeric cis and trans alcohols of Formulas (I) through (IV) below:

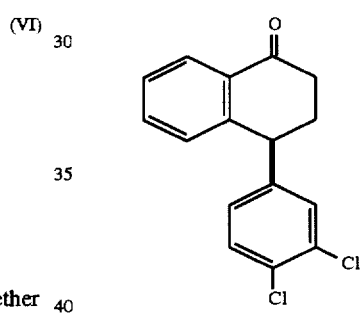

B

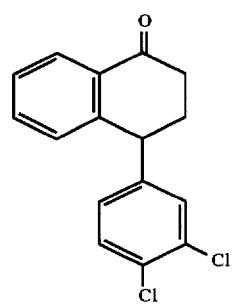

A

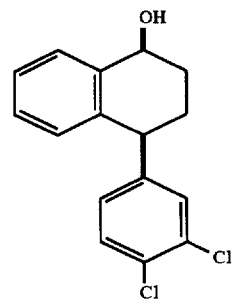

I

-continued

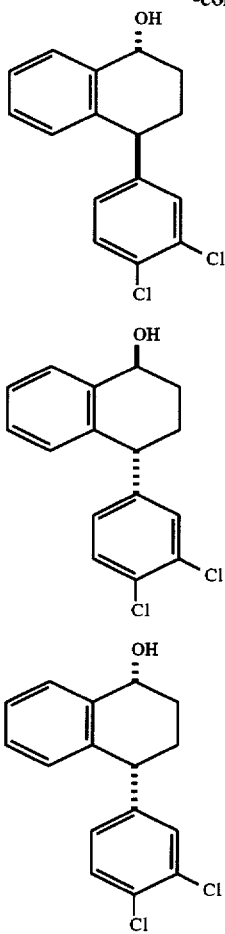

by reacting said racemic 4-(3,4-dichlorophenyl)-3,4-dihydro-1(2H)-naphthalenone with one or more asymmetric ketone reducing agents comprising enantioselective organoborane reagents independently selected from the group consisting essentially of:

(1) a chiral oxazaborolidine of Formula (V) or (Va) below:

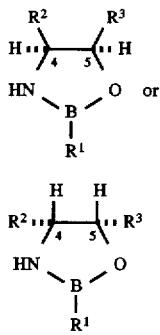

wherein:

$R^1$ is hydrogen, ($C_1$–$C_8$) alkyl, benzyl, phenyl or phenyl substituted with up to three substituents independently selected from the group consisting essentially of ($C_1$–$C_8$) alkyl, ($C_1$–$C_8$) alkoxy and halo; and $R^2$ and $R^3$ are syn and the same and are each phenyl or phenyl substituted with up to three substituents independently selected from the group consisting essentially of ($C_1$–$C_8$) alkyl, ($C_1$–$C_8$) alkoxy and halo; and a source of borane is additionally present;

(2) a chiral oxazaborolidine of Formula (VI) below:

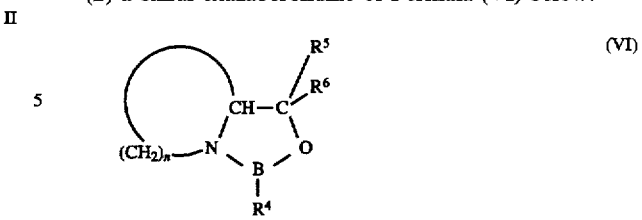

wherein:

$R^4$ is hydrogen, ($C_1$–$C_8$) alkyl, or aryl ($C_1$–$C_8$) alkyl;

n is 2, 3, or 4, such that the group $(CH_2)_n$ forms, together with the oxazaborolidine nitrogen and adjacent carbon, a 4-, 5-, or 6-membered ring; and a source of borane is additionally present; and $R^5$ and $R^6$ are phenyl; and (3) either enantiomer of a compound of Formula (D) below:

$Ipc_2BX$ (D)

wherein:

Ipc is isopinocampheyl;

B is boron; and

X is halo;

B. separating cis alcohol of Formula (I) from trans alcohol of Formula (III) and oxidizing said cis alcohol of Formula (I) to yield said chiral (4S)-(3,4-dichlorophenyl)-3,4-dihydro-1(2H)-naphthalenone of Formula (B); and C. separating cis alcohol of Formula (IV) from trans alcohol of Formula (II) and oxidizing said trans alcohol of Formula (II) to yield said chiral (4S)-(3,4-dichlorophenyl)-3,4-dihydro-1(2H)-naphthalenone of Formula (B).

15. A compound of the formula:

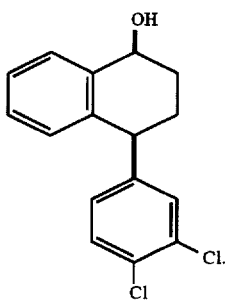

(I)

16. A compound of the formula:

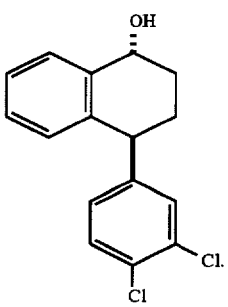

(II)

17. A compound of the formula:
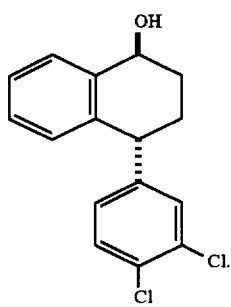
(III)
18. A compound of the formula:
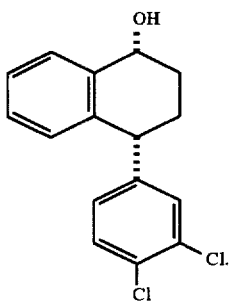
(IV)
* * * * *